United States Patent [19]
Gerber et al.

[11] Patent Number: 5,737,086
[45] Date of Patent: Apr. 7, 1998

[54] APPARATUS AND METHOD FOR SPECTROSCOPIC MEASUREMENT AS A DEFLECTION OF A BIMORPH CARRYING A SAMPLE THAT IS HEATED BY RADIATION

[75] Inventors: Christoph Gerber, Richterswil; James Kazimierz Gimzewski, Rueschlikon; Bruno Reihl, Wilen; Räto Rudolf Schlittler, Schoenenberg, all of Switzerland

[73] Assignee: International Business Machines Corporation, Armonk, N.Y.

[21] Appl. No.: 571,868

[22] PCT Filed: Jan. 27, 1994

[86] PCT No.: PCT/EP94/00224

§ 371 Date: Apr. 24, 1996

§ 102(e) Date: Apr. 24, 1996

[87] PCT Pub. No.: WO95/02170

PCT Pub. Date: Jan. 19, 1995

[30] Foreign Application Priority Data

Jul. 6, 1993 [EP] European Pat. Off. ............ 93/01742

[51] Int. Cl.[6] ...................................................... G01N 25/34
[52] U.S. Cl. ............................................................. 356/432
[58] Field of Search ............................... 356/216, 432 T

[56] References Cited

U.S. PATENT DOCUMENTS

| | | | |
|---|---|---|---|
| 3,887,937 | 6/1975 | Gatos et al. | 357/26 |
| 4,184,768 | 1/1980 | Murphy et al. | 356/216 |
| 4,762,426 | 8/1988 | Foss | 374/130 |
| 5,003,815 | 4/1991 | Martin et al. | 73/105 |
| 5,545,897 | 8/1996 | Jack | 356/437 X |

FOREIGN PATENT DOCUMENTS

| | | |
|---|---|---|
| 0067574 | 12/1982 | European Pat. Off. . |
| 875881 | 5/1953 | Germany . |
| 2011612 | 7/1979 | United Kingdom . |
| 2169418 | 7/1986 | United Kingdom . |

OTHER PUBLICATIONS

Umeda et al, "Scanning Attractive Force Microscope using Photothermal Vibration", J. Vac. Sci. and Technology, B9(2) Mar./Apr. 1991.

*Primary Examiner*—Vincent P. McGraw
*Attorney, Agent, or Firm*—Ronald L. Drumheller

[57] ABSTRACT

A spectrometer is described with a new intensity detector for electromagnetic radiation. The detector comprises means for detecting the deflection of a cantilever which has a bimetallic/bimorph structure. The deflection is proportional to the absorbed amount of radiation.

9 Claims, 6 Drawing Sheets

APPARATUS AND METHOD FOR SPECTROSCOPIC MEASUREMENT AS A DEFLECTION OF A BIMORPH CARRYING A SAMPLE THAT IS HEATED BY RADIATION

The invention relates to a spectrometer, in particular to the light intensity detectors in a spectrometer, and its use.

BACKGROUND OF THE INVENTION

Spectrometers or spectroscopes are defined as instruments for analyzing the spectral energy distribution of electromagnetic radiation. They generally incorporate a source or sources of electromagnetic radiation, a dispersing system or monochromator, and a detector monitoring the intensity of the electromagnetic radiation. The known spectrometers are designed for a broad range of the electromagnetic spectrum. Spectrometers for recording x-ray, ultraviolet (uv), visible (vis), infrared, or microwave, adsorption and emission spectra can be found.

After the dispersion of light was discovered by Newton almost three centuries ago, spectroscopes went through a tremendous development. All aspects of the fundamental spectrometer, as described above, through all its variants and differing fields of application are covered by numerous publications. Yet, none of these can be considered to be particularly close to the current invention, as far the applicant is aware of.

Another technical field, being of importance to the current invention, is known as scanning probe microscopy, though no ordinary person skilled in the art would consider it to be related to the technical field of spectroscopy. To the best knowledge of the applicant, no direct relationship between both technical fields has been so far established.

The scanning probe microscopy, the most prominent representative of which is known as scanning tunneling microscope or STM, is accepted since its first publication by G. Binnig, H. Rohrer, Ch. Gerber, and E. Weibel in: Phys. Rev. Lett. 49, p. 59 (1982) as a valuable tool for imaging surfaces with atomic resolution. The concept of the STM was further developed to another type of microscope with atomic resolution, the atomic force microscope or AFM. The first description of an AFM was published in: Phys. Rev. Lett. 56, p. 930–933 (1996) by G. Binnig, C. F. Quate and Chr. Gerber.

The basic setup for an AFM involves the use of a flexible element to which a scanning tip or microprobe is attached. This flexible element is generally called cantilever and is, for example, made by silicon micromanufacturing. In operation, the tip is scanned over the surface of a sample. When the tip comes closer to the surface, it experiences forces which cause the cantilever to bend. The deflection of the cantilever is then monitored and converted into a 'force' image of the surface.

A third element of importance to the current invention is the so-called bimetal or thermobimetal effect: two stripes of metal being thightly bonded or welded will bend when being subjected to heating. The bimetal effect has been brought into connection to the field of AFM by 0. Marti et al. in: Ultramicroscopy 42–44 (1992), pp. 345–350. It is, however, described merely as a source of nuisance to those working in this area.

With regard to the numerous efforts aimed at improving the sensitivity and handling of spectrometers or spectroscopes. It is an object of the invention to provide a new spectrometer. It is a particular object of the invention to provide the known types of spectrometer with a new sensitive device for measuring the intensity of electromagnetic radiation.

SUMMARY OF THE INVENTION

The new spectrometer or spectroscope comprises at least one source of electromagnetic radiation, monochromator means for selecting a sharply defined range of said electromagnetic radiation, and means for detecting the intensity of said electromagnetic radiation, wherein said means comprises a flexible element with a least two layers of material having a different thermal expansion coefficient and means to detect a deflection of said flexible element. The new sensor is based on what is commonly known as bimetal or thermobimetal effect. Bimetal switches have found a wide spread application in many devices, though being more and more replaced by electronic devices. In principle, a bimetallic temperature sensor is made of two tightly bonded layers of materials differing in their respective thermal expansion coefficient. These materials do not necessarily have to be metals. Therefore, the term "bimorph" is used as a less known but more precise synonym for "bimetallic". In case of a temperature change, both material elongate by different amounts, thus, introducing a bending or deflection of the flexible element from its original shape or position. In a first approximation, the bending radius of a thin bimorph strip is given by $R=l/(\alpha_1-\alpha_2)\Delta T$ with $l$ being the length of the strip, $\alpha_1, \alpha_2$ being the respective thermal expansion coefficients of the two bonded materials, and $\Delta T$ being the temperature difference. The known bimetallic devices, however, have sizes within the centimeter range, making them unacceptable for any use besides a crude temperature measurement. Though the invention makes use of the bimetallic effect, the dimensions of the new device are reduced to below one millimeter, reducing simultaneously the thermal capacity and the heat flow out of the device and, thus, enhancing the sensitivity of the device.

As for the materials, themselves, there are, in principle, no constraints upon the shape of the flexible element used in the new device. However, to enhance sensitivity, it has preferably a beamlike shape or is formed like a triangle with a punched central portion, in which the length surmounts the width by approximately a factor of 10. Calculations based on the simple case of a beam as flexible element show that an optimum sensitivity can be achieved by using long thin beams. However, thermally induced noise makes it desirable to utilize a flexible element with a spring constant of above 1 N m$^{-1}$ and a high resonance frequency. These conditions, together with a demand for a fast response time, enable a skilled person to optimize the new sensor in accordance with any imposed requirement.

A further enhancement of the sensitivity of the flexible element can be achieved by using more refined designs, e.g. by separating the two layers with different expansion coefficients leaving only at a few points bridges as a connection. However, these flexible elements have to be prepared with higher accuracy than the simple elements described above. As the silicon technology is the most developed technology for producing miniaturized devices, it is of advantage to use materials based on silicon for the preparation of the bimorph flexible elements. For example, Petersen describes in the IEEE Transactions on Electron Devices, Vol.ED-25, No. 10, October 1978,pp. 1241–1250, the preparation of metal coated cantilevers on silicon wafers. From other sources, the preparation of beams of SiN by anisotropic chemical etching is known. Other feasible methods for preparing the desired flexible element are focussed beam techniques, reactive ion etching, and x-ray or synchrotron lithography in combination with galvano- or electroforming.

The second layer has advantageously a thermal expansion coefficient $\alpha_2$ which differs substantially from the thermal expansion coefficient $\alpha_1$ of the main material of the flexible element. Suitable materials are, for example, metals like Al and Au, which are easily applicable onto the surface of Si and SiN.

To make the bimorph or "bimetallic" element a tool for transmission spectroscopy, the layers can be manufactured by using transparent material of different thermal expansion coefficients, such as fused Silica and borosilicate glass (PYREX).

Several accurate methods to detect the bending of a cantilever are known from the field of atomic force microscopy (AFM). The AFM is known as a device to examine the roughness of a surface. For that purpose, a cantilever is applied with a microscopic tip and scanned across the surface to be examined. It is found that the methods applied in AFM to detect the deflection of the cantilever can be advantageously employed in the new device. With the help of these methods, lever deflections of the order of less than 1 nm can be easily detected. In addition, motions of the lever ranging from 0.001 nm up to 100 µm can be monitored, giving the new sensor a possible dynamic range of $10^9$. It is well within the scope of an averaged skilled person to choose one of the available methods known in the field of atomic force microscopy as means to detect the deflection of the flexible element.

One group of these detecting methods is based on coupling the cantilever to another distance sensitive microscope. A combination of the cantilever with a scanning tunneling microscope is described, for example, in the patent U.S. Pat. No. 4,724,318. Another approach using an evanescent wave coupling sensor, also known as scanning near-field optical microscope (SNOM) or scanning tunneling optical microscope (STOM), is described by Diaspro and Aguilar in: Ultramicroscopy 42–44 (1992), pp. 1668–16.

Another group of detecting methods is based on the well known piezoelectric or piezoresistive effect. An example is described in: M. Todonese et al., Appl. Phys. Lett. 62 (8), 1993, pp. 834–836. These methods provide detection schemes in which the deflection detector is integrated in the cantilever. Yet another feasible way of detecting the displacement of the cantilever relies on capacitance sensing and is known, for example, from Joyce et al., Rev. Sci. Instr. 62(1991), p. 710, and Goddenhenrich et al., J. Vac. Sci. Technol. A8 (1990), p. 383.

It is also possible to use the changes in the resonance frequencies of the flexible element to measure its bending. The fundamentals of this technique are known and described for example in the patent U.S. Pat. No. 3,413,573. The displacement of the flexible element can also be measured by applying optical methods, such as beam deflection or interferometry. The beam deflection method makes use of the length of the lever. Usually, a light beam, preferably produced by a laser diode or guided through an optical fiber, is directed onto the lever. A small deflection of the lever causes a reasonable change in the reflecting angle and, therefore, results in a deflection of the reflected light beam that is measured with bicell or other suitable photo detectors. The beam deflection method is simple and reliable. Interferometric methods are described, for example, by Martin et al., J. Appl. Phys. 61(1987), p. 4723, by Sarid et al., Opt.Lett. 12 (1988), p. 1057, and by Oshio et al., Ultramicroscopy 42–44 (1992), pp. 310–314.

Advantageously, the flexible element comprises a chemical sensing layer, which may be one of two "bimetallic" layers. However, in most cases it will be applied as a third, distinct layer. The term "chemical sensing" is used in its broadest meaning, including a sensitivity for the photons of the electromagnetic radiation, i.e. for the electromagnetic field. Particularly preferred is a layer with a high absorption over a broad range of wavelengths, i.e., a black layer, or a layer having a specifically high absorption in a particular wavelength region. Further types of the sensing layer are described below.

The flexible element, however, does not necessarily comprise a layer of the sample, as one might be inclined to believe. When analyzing a gaseous sample or of a sample stored in a separate container, no layer of the sample might be found on the flexible element itself.

For increasing the path of the radiation through a sample, a technique which enhances the sensitivity of the spectroscope, the sample may be cladded between two reflecting layers.

It is a particular advantage of the invention that the high sensitivity of the new detection scheme and its good response over the entire electromagnetic spectrum allow to replace known radiation detectors, such as vacuum photodiodes, photomultipliers, photocathodes, photoconductors, photodiodes, thermopiles, pyroelectric detectors, bolometers or golay cells, in known spectrometers. A device according to the invention may replace a known detector without changing the basic setup of the other parts of the spectrometer. Thus, the same sources of radiation, e.g., (tuneable) continuous or pulsed lasers or laser diodes, discharge type lamps, blackbody sources like the Globar or tungsten-filament lamps, flashlamps, or tuneable high frequency oscillators or klystrons, can be used. Also the dispersing means or monochromators, of which prisms, interference filters, or gratings are only the most prominent examples, are applicable in an unchanged manner.

In another embodiment of the invention, specifically designed to analyze chemical reactions or to attract or trap specific molecules, the flexible element comprises a catalysts or an ad/absorbent as chemical sensing layer.

An ideal catalyst is defined as a substance that increases the rate at which a chemical reaction approaches equilibrium, without itself becoming permanently affected by the reaction. The catalyst achieves this enhancement by providing an alternative reaction path, involving different activated complexes, with a lower activation energy than the uncatalysed reaction mechanism. A wide range of catalysts for many different chemical reactions is known. For measurements using the catalytic oxidation of hydrogen, carbonmonoxide, hydrocarbons and other combustible gases, for example, the transition metals Pt, Pd, Rh, Ir, or their oxides, or a mixture of those materials are preferably applied.

It is possible to provide a surface of the cantilever with a thin layer by using known deposition techniques, such as sputtering, epitaxial methods or electrochemical deposition. The surface of a deposited film can be further enlarged or roughened by etching with a suitable chemical agent.

As said above, the chemical sensing layer may also be a material which enables a chemisorption, i.e. the formation of chemical bonds between the (surface) molecules of said layer and those molecular species to be examined by the new spectrometer, or adsorption. Suitable materials are, for example, Ni, Fe, Ag, and Pt.

By being able to detect chemisorption and adsorption, the new spectrometer also forms a valuable device to monitor biochemical processes. The sensing layer is this case is advantageously a Langmuir-Blodgett (LB) film applied to the bimorph cantilever by known methods. Using the defined hydrophilic or hydrophobic surface of the LB film and the affinity between certain molecules, such as proteins and enzymes, it is possible to tailor a highly specific sensor suitable not only for gas analysis but also for medical test methods, e.g. immunoassay systems. The vast state of ad concerning LB films is, for example, referred to in: G. G. Roberts (ed.), Langmuir-Blodgett Films, Plenum, New York, 1990. A method for applying a LB film to the surface of a semiconducting surface is detailed by S. Lee et al., Sensors and Actuators B, 12 (1993), pp. 153–154.

Many catalytic reactions equally require an initial temperature. The difference in the initial temperature allows to inhibit and suppress undesired reactions. These temperature dependent reactions can be effectively monitored using the spectrometer. In general, it is more convenient to provide the necessary temperature by heating the sensing layer than by heating the reactants, themselves. As to this reason, the sensor preferably comprises a heating device for the sensing layer. The sensing layer can be heated by a juxtaposed electrical heater, i.e. a thermoelement, or by using electromagnetic radiation.

In a preferred embodiment of the invention, the sensing layer is heated by the same light emitting device which is employed for measuring the deflection of the flexible element by using the above described beam deflection method. The sensitivity of the new spectrometer is enhanced by employing a pair of flexible elements only one of which is covered by the sample to be analyzed. This embodiment of the invention has intrinsic reference or calibration properties, as both levers bend by the same amount for temperature changes not related to the absorption of radiation by the sample.

By using a second flexible element, covered with a substance with a known absorption or reflection spectrum (depending on whether the spectrometer is used for absorption or reflection measurements) and irradiating both by the same source, it is possible to compensate for changes in the intensity of the radiation as emitted from this source. Ideally, only the differential signal can be determined to give the spectrum of the sample with increased accuracy. By combining levers coated with different chemical sensing layers and/or levers held at different temperatures, it is possible to manufacture an artificial nose, able to spectroscopically identify and analyze different specimens in parallel. Interferences between several substances may be eliminated by applying multicomponents analysis techniques known per se.

These and other novel features believed characteristic of the invention are set forth in the appended claims. The invention itself however, as well a preferred mode of us, and further objects and advantageous thereof, will best be understood by reference to the following detailed description of illustrative embodiments when read in conjunction with the accompanying drawings.

DESCRIPTION OF THE DRAWINGS

The invention is described in detail below with reference to the following drawings.

EXAMPLES

Figure 1:
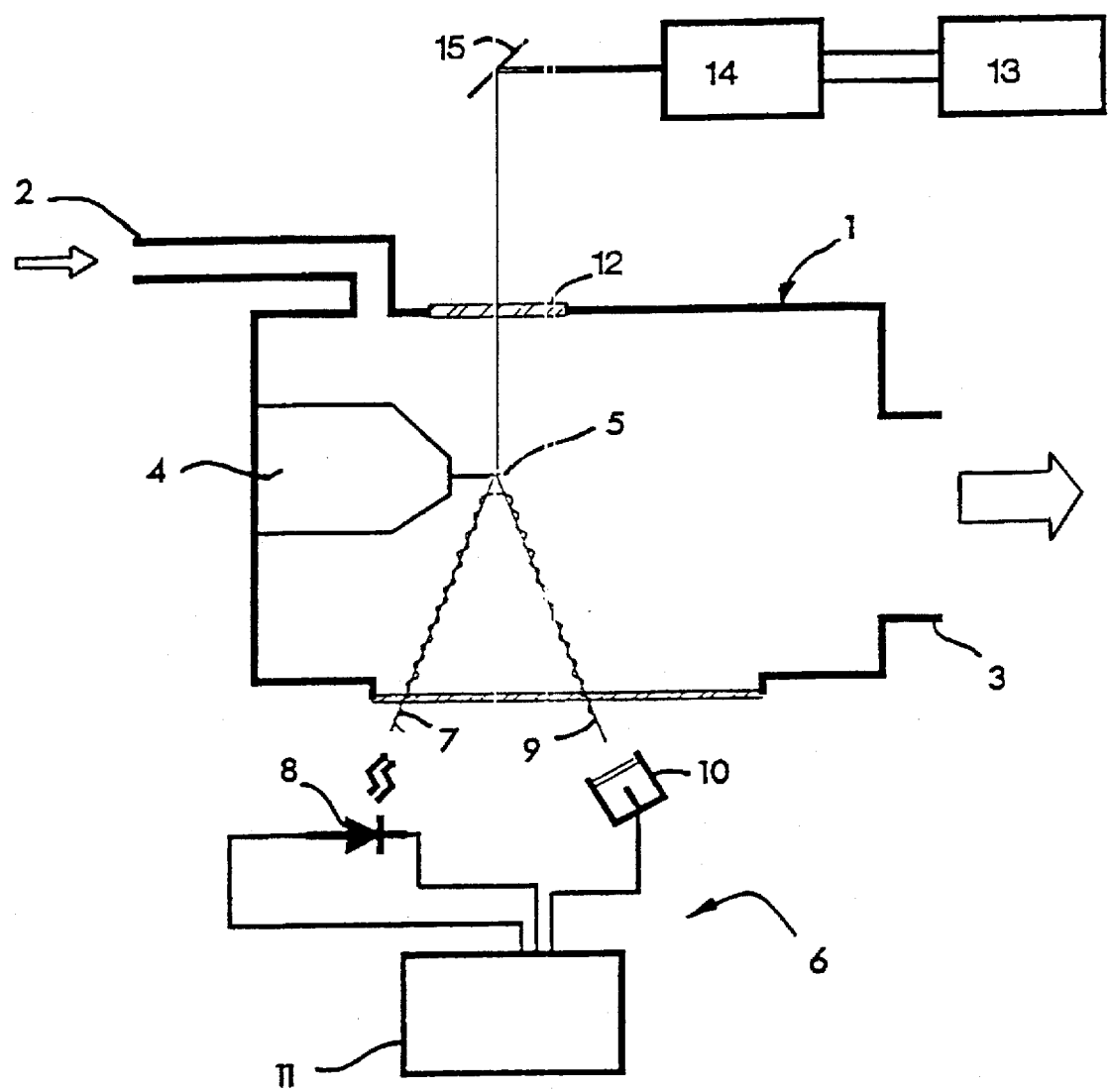
FIG. 1 schematically shows a possible embodiment of the new spectrometer.

An embodiment of the spectrometer according to the invention can be built by using parts of a conventional atomic force microscope (AFM). FIG. 1 shows a vacuum chamber 1, an inlet 2 for test gas mixtures and an outlet 3 leading to the pumping system (not shown). The chamber 1, further, comprises a holder 4 to mount the flexible element, the cantilever 5 which serves as such flexible element, and a beam deflection system 6 for determining the deflection of the cantilever 5. A light beam 7 is generated by a laser diode 8. In operation, the beam 7 is reflected from the cantilever 5 and the reflected beam 9 is surveilled by two sectors of a quadrant detector 10. The quadrant detector is operated in the (A–B)/(A+B) mode to normalize for fluctuations in the laser power. The beam deflection system comprises means 11 to determine the deflection of the cantilever 5 using the signals received the detector 10.

The described AFM is coupled to a light source 13, having a monochromator 14, via a deflecting mirror 15 and a light entry opening or window 12 at the top of the chamber 1. Thus, pads of conventional spectrometers are easily applied in this embodiment.

To demonstrate the operating principle of the new spectrometer, a high-pressure Argon discharge lamp is chosen as light source for the ultraviolet wavelength region. The path of the light beam and the chamber is continuously kept under vacuum for the uv measurement.

Figure 2A:
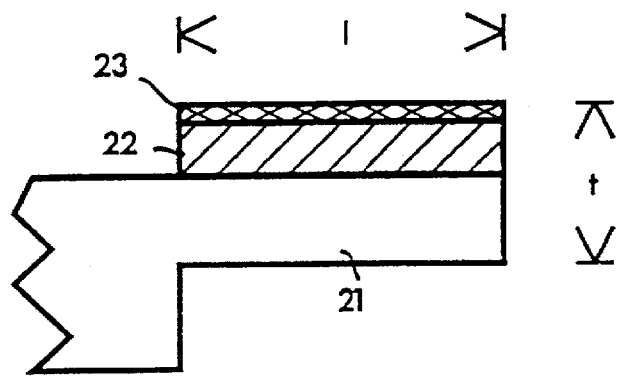
FIGS. 2A, B, C show a component of the new spectrometer in different embodiments.
Figure 2C:
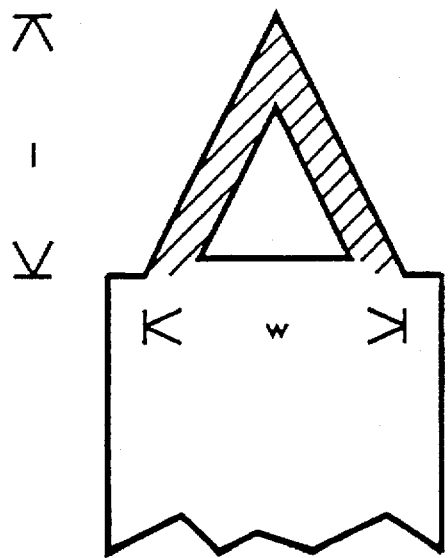
Figure 2B:
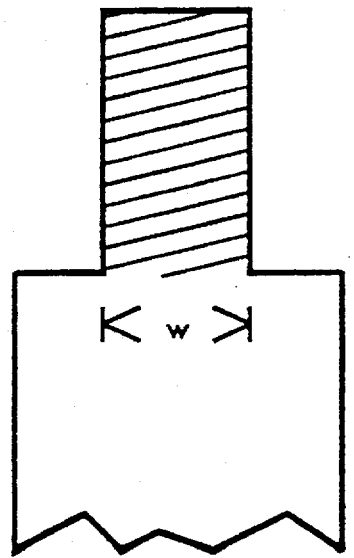

As a light detecting device, a beam-shaped bimorph cantilever, as shown in FIGS. 2 A, B, is employed. The cantilever's base material 21 is Silicon with a thickness of 1.5 µm coated by a 0.4 µm thick layer 22 of Al using a vacuum evaporation technique. Both layers 21, 22 have thermal expansion coefficients $\alpha_1, \alpha_2$ which differ significantly as having the values $3 \times 10-6°$ C.–1 for Si and $25 \times 10-6°$ C.–1 for Al. The layers 21, 22, thus, form the desired bimorph or "bimetallic" junction. Using again vacuum evaporation, a 40 nm thick Pt layer 23 is deposited on top of the AL layer. The overall dimensions of the applied cantilever are: l=400 µm, w=35 µm, and t=1.94 µm.

Figure 3:
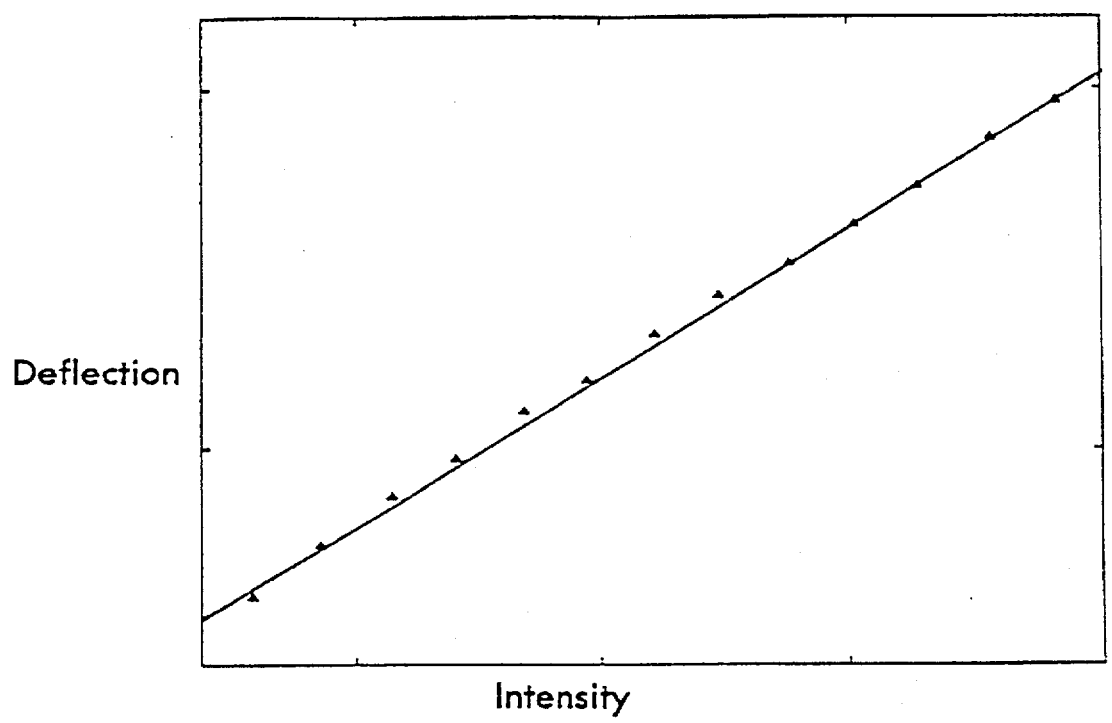
FIG. 3 shows a calibration curve of the radiation intensity versus the deflection of a flexible element as caused by said radiation.

A light intensity versus deflection curve is measured to provide a calibration of the spectrometer. As shown by FIG. 3, the deflection of the bimorph cantilever relates linear to the heat transfer induced by radiation of a laser diode emitting a variable intensity. The data further show that an effective heating of the cantilever can be achieved by using the laser radiation of the deflection beam system. Thus, it is possible to heat the Pt layer 23 above the ambient temperature.

By measuring the response of the cantilever 5 to a laser pulse of 300 µW, a response time of approximately 1 ms is determined for a device according to the example.

Figure 4A:
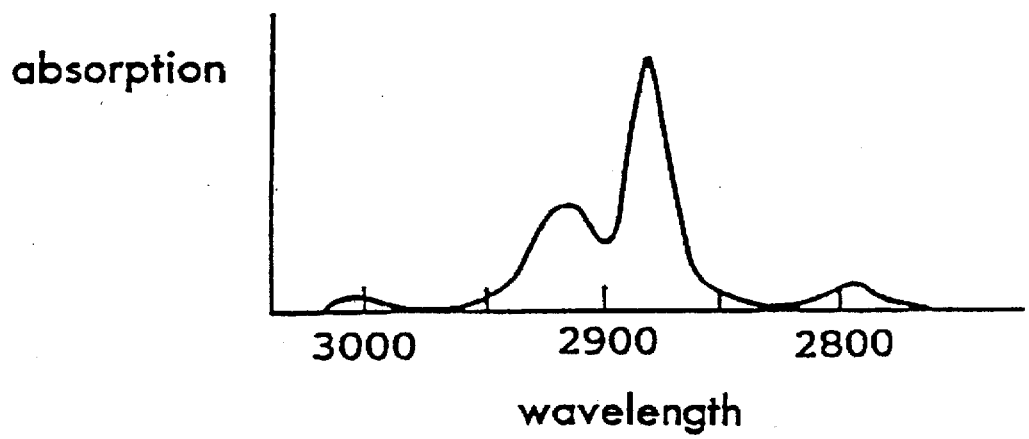
FIGS. 4A, B show possible results of spectroscopic measurements.
Figure 4B:
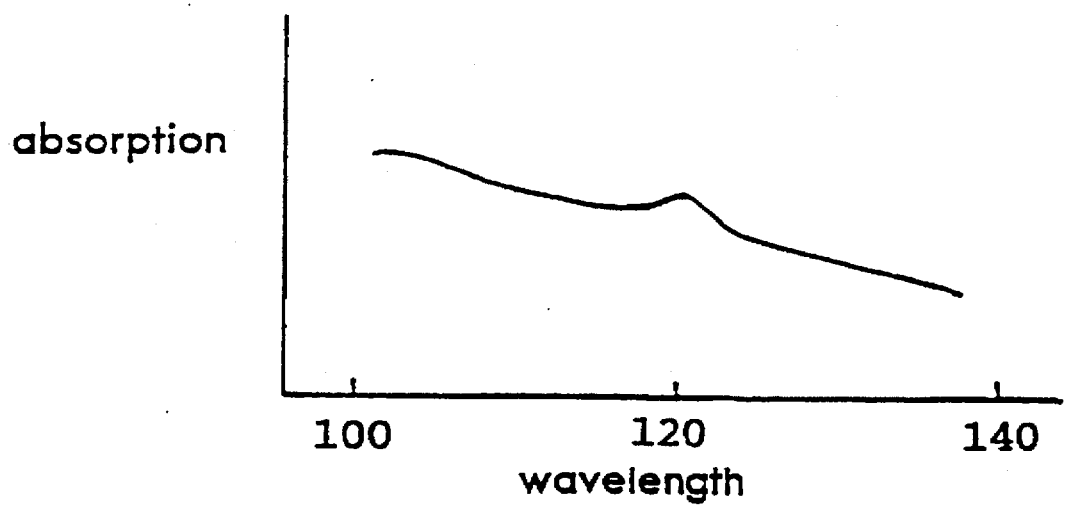

Taking into account the variations of the intensity emitted by the applied light source over the wavelength range, an absorption spectrum of the platinum layer as shown by FIG. 4B can be measured. The absorption is given in arbitrary units (a.u.). The measurement covers a wavelength range from 100 nm to 165 nm. It shows a peak around 120 nm.

In another example, a triangularly shaped cantilever 5 is used as illustrated by FIGS. 2 A, C. The cantilever's base material 21 is silicon nitride (SIN), coated by a 0.2 µm thick layer 22 of Al using vacuum evaporation. Using the same technique, again, a layer 23 of Pt is deposited onto the aluminum. The layer 23 has a thickness of 20 nm. As in the previous example, fine intermediate layers formed by the oxidation of the freshly etched or deposited surface are not taken into account as separate layers. The dimensions (see FIGS. 2A, C) of the cantilever are: l=200 μm, w=20 μm, and t=2 μm with a force constant of approximately 0.1 $Nm^{-1}$. A layer of ethylene (not shown) is deposited by an adsorption process as a sample onto the platinum layer 23. In this example, a infrared light source (Globar) from a commercially available ir-spectrometer is applied, together with its monochromator. FIG. 4A shows the resulting absorption spectrum having peaks at approximately 3000 $cm^{-1}$, 2880 $cm^{-1}$, 2920 $cm^{-1}$, and 2810 $cm^{-1}$.

Figure 5:
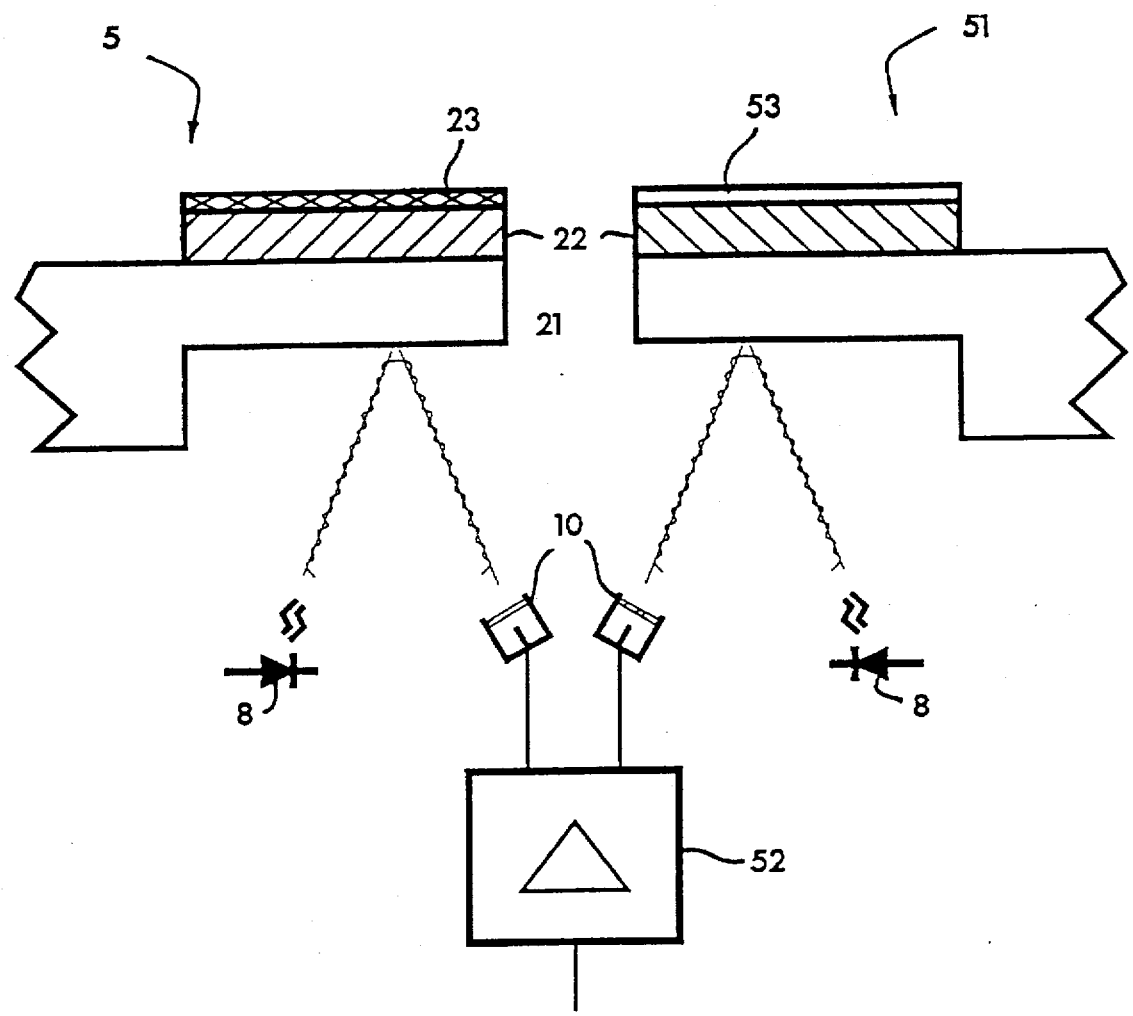
FIG. 5 shows basic components of a spectrometer suitable for differential measurements.
Figure 6:
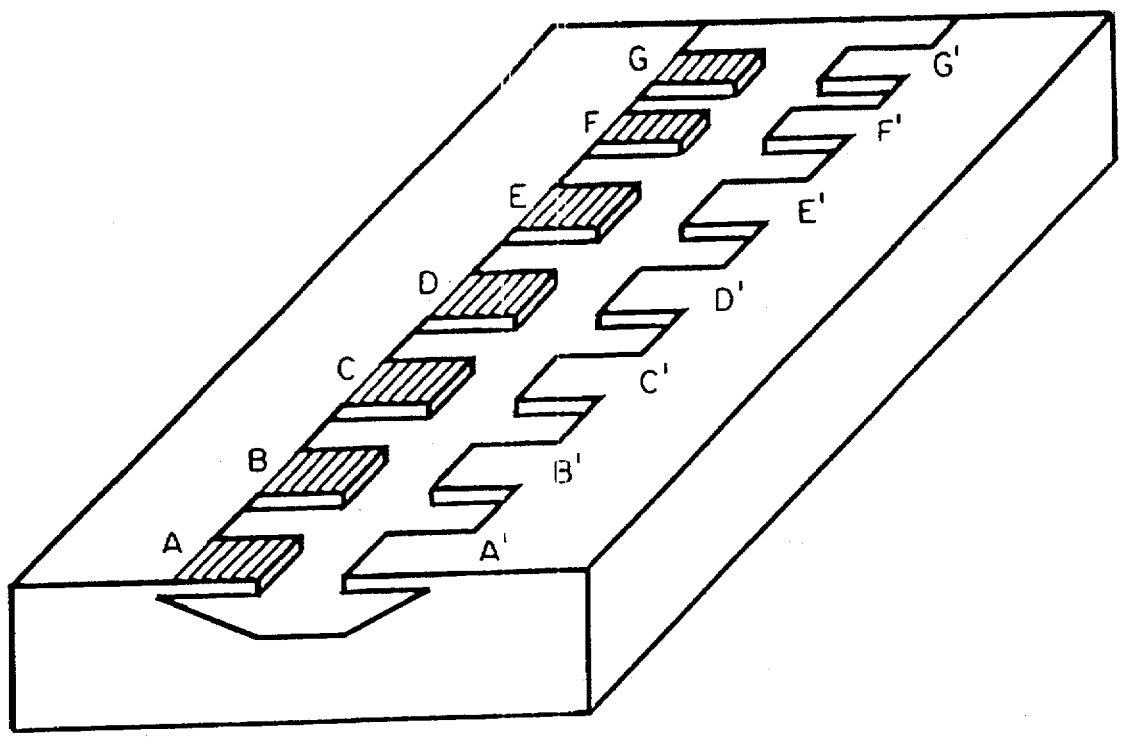
FIG. 6 shows a basic components of a spectrometer suitable for simultaneous measurements of several samples.

It is further possible to enhance the sensitivity of the spectrometer by eliminating some of the background noise (temperature shifts, etc.) and by compensating for variations of the intensity of the electromagnetic radiation as emitted by the source. An example of such a device with an intrinsic calibration is shown in FIG. 5. It comprises a second lever 51' almost identical to the first lever 5 covered, however, by a layer 53 with a known absorption or reflection, depending on whether the spectrometer is used for absorption or reflection measurements. Both levers are irradiated by the same beam. The deflection of each lever is measured with the same means 6 as described above (see FIG. 1), additionally comprising means 52 to determine the differential spectrum by measuring the deflections of both levers and taking the known absorption spectrum of the reference lever 51 into account. By coupling several sensors (with intrinsic calibration), each sensitized to a different species A, B, C, D, E, F, and G, as illustrated by FIG. 6, a multi-component analyzer is realized. Letters A', B'... and G' denote reference levers used to eliminate the background noise. Though a careful choice of suitable chemical sensing layers and wavelength regions has to be made by a skilled person, the fundamental principles of the device remains unchanged. Simultaneous measurements can be performed at the components for which the levers have been sensitized. Interferences occurring due to a partial sensitivity of a layer for more than one species can be filtered out by an appropriate mathematical method.

As all components of the intensity detecting device (levers, laser diodes, photo detectors, etc.) are producable on the semiconducting base material (Si), it is readily feasible to manufacture also large arrays of the sensor on a single-chip basis.

We claim:

1. A spectrometer with at least one source of electromagnetic radiation, monochromator means for selecting a defined wavelength or wavelength range of said electromagnetic radiation, a flexible element having a sample of interest on or within said flexible element, means for irradiating said sample with said selected electromagnetic radiation, said sample and flexible element being heated by absorption of said selected electromagnetic radiation by said sample, and means for measuring a deflection of said flexible element, said flexible element having at least two layers of materials with different thermal expansion coefficients so that said flexible element deflects when heated by absorption of said selected electromagnetic radiation by said sample, said measured deflection of said flexible element being a measurement of the absorption of said selected electromagnetic radiation by said sample.

2. Spectrometer in accordance with claim 1, wherein the means for measuring the deflection of the flexible element is a light beam deflection means.

3. Spectrometer in accordance with claim 1, wherein the flexible element carries the sample as a sensing layer separate from said at least two layers having different thermal expansion coefficients.

4. Spectrometer in accordance with claim 3, wherein the sensing layer is a layer having a high absorption over a wide range of wavelengths, and/or constitutes the material to be analyzed, and/or is a catalyst, ab- or adsorbent, and/or consists of an organic material, preferably as a Langmuir-Blodgett film.

5. Spectrometer in accordance with claim 1, further comprising means for compensating a background deflection of the flexible element and/or fluctuations in the intensity of said electromagnetic radiation.

6. Spectrometer in accordance with claim 5, wherein the compensating means comprises a pair or an array of flexible elements, at least one of which serves as reference, said reference including a layer with high absorption or high reflectivity over a broad range of wavelengths, means for determining the deflections of said flexible elements, and further means for determining at least one differential spectrum.

7. Spectrometer in accordance with claim 1, comprising an array of flexible elements, covered with different (chemical) sensing layers.

8. Spectrometer in accordance with claim 1, comprising a second flexible element which serves as a reference with respect to which the deflection of the flexible element having the sample is measured.

9. Method for spectroscopic measurements of a sample, comprising the steps of:

carrying the sample upon or within a flexible element having at least two layers of materials with different thermal expansion coefficients so that the flexible element deflects when heated;

irradiating the sample with a beam of electromagnetic radiation, the sample and the flexible element carrying the sample being heated by absorption of the electromagnetic radiation by the sample, the flexible element thereby deflecting; and measuring the deflection of the flexible element as a measurement of the absorption of the electromagnetic radiation by the sample.

\* \* \* \* \*